US012678576B2

(12) United States Patent
Eger et al.

(10) Patent No.: US 12,678,576 B2
(45) Date of Patent: Jul. 14, 2026

(54) PROCESS AND APPARATUS FOR MONITORING A VENTILATOR

(71) Applicant: Drägerwerk AG & Co. KGaA, Lübeck (DE)

(72) Inventors: Marcus Eger, Lübeck (DE); Thomas Handzsuj, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 845 days.

(21) Appl. No.: 18/064,388

(22) Filed: Dec. 12, 2022

(65) Prior Publication Data

US 2023/0191056 A1     Jun. 22, 2023

(30) Foreign Application Priority Data

Dec. 16, 2021     (DE) ..................... 10 2021 133 485.3

(51) Int. Cl.
*A61M 16/00*          (2006.01)

(52) U.S. Cl.
CPC ...... *A61M 16/024* (2017.08); *A61M 16/0051* (2013.01); *A61M 2230/40* (2013.01)

(58) Field of Classification Search
CPC .... A61N 16/00; A61N 16/022; A61N 16/024; A61N 16/026
See application file for complete search history.

(56) References Cited

U.S. PATENT DOCUMENTS

| | | | |
|---|---|---|---|
| 9,392,964 B2 | 7/2016 | Mulqueeny et al. | |
| 10,874,811 B2 | 12/2020 | Gholami et al. | |
| 11,478,594 B2 * | 10/2022 | Li | A61M 16/204 |
| 2014/0034054 A1 * | 2/2014 | Angelico | A61M 16/0069 |
| | | | 128/204.23 |
| 2014/0296728 A1 * | 10/2014 | Sinderby | A61B 5/086 |
| | | | 600/529 |

(Continued)

FOREIGN PATENT DOCUMENTS

| | | |
|---|---|---|
| EP | 3274031 B1 | 3/2020 |
| EP | 2779896 B1 | 9/2020 |

(Continued)

OTHER PUBLICATIONS

Blanch, L., Villagra, A., Sales, B. et al.: Asynchronies During Mechanical Ventilation are Associated with Mortality. Intensive Care Med. 41: 633 641 (2015).

(Continued)

*Primary Examiner* — Joseph D. Boecker
*Assistant Examiner* — Jaeick Jang
(74) *Attorney, Agent, or Firm* — McGlew and Tuttle, P.C.

(57)          ABSTRACT

A process and apparatus monitor a ventilator (100). The ventilator (100) performs supportive artificial ventilation including a sequence of ventilation strokes, with the objective that each inspiration effort of the patient (Pt) triggers a ventilation stroke and the start and the end of the ventilation stroke coincide with the start and the end of the inspiratory effort, respectively. A monitoring unit (11) detects deviations between the patient's own inspiratory efforts and the artificial ventilation and determines a respective measure for the respective frequency and/or duration for different possible asynchrony types.

16 Claims, 6 Drawing Sheets

(56) References Cited

U.S. PATENT DOCUMENTS

2016/0325061 A1    11/2016  Tams et al.
2018/0078721 A1*    3/2018  Jalde ...................... A61B 5/285

FOREIGN PATENT DOCUMENTS

WO         2013071404  A1    5/2013
WO         2021074747  A1    4/2021

OTHER PUBLICATIONS

Sinderby C, Liu S, Colombo D, Camarotta G, Slutsky AS, Navalesi P, Beck J.: An Automated and Standardized Neural Index to Quantify Patient-Ventilator Interaction. Crit Care. 17(5):R239 (2013).
Dres M, Rittayamai N, Brochard L.: Monitoring Patient-Ventilator Asynchrony. Curr Opin Crit Care. 22(3):246-253 (2016).
Akoumianaki E, Lyazidi A, Rey N, Matamis D, Perez-Martinez N, Giraud R, Mancebo J, Brochard L, Richard JM. Mechanical Ventilation-Induced Reverse-Triggered Breaths: A Frequently Unrecognized form of Neuromechanical Coupling. Chest. 143(4):927-938 (2013).
Piquilloud L. et al.: Neurally Adjusted Ventilatory Assist Improves Patient-Ventilator Interaction. Intensive Care Med. 37: 263-271 (2011).

\* cited by examiner

PROCESS AND APPARATUS FOR MONITORING A VENTILATOR

CROSS REFERENCE TO RELATED APPLICATIONS

This application claims the benefit of priority under 35 U.S.C. § 119 of Application 10 2021 133 485.3, filed Dec. 16, 2021, the entire contents of which are incorporated herein by reference.

TECHNICAL FIELD

The invention relates to a monitoring process and apparatus for automatically monitoring a ventilator.

BACKGROUND

A ventilator is capable of artificially ventilating a patient. The patient is typically connected to a patient-side coupling unit, such as a breathing mask on the patient's face or a tube or catheter in the patient's body. The ventilator is at least temporarily in fluid communication with the patient-side coupling unit and performs a sequence of ventilation strokes. During each ventilation stroke, an amount of a gas mixture comprising oxygen is delivered to the patient-side coupling unit and further into the patient's body.

In a first type of artificial ventilation, the gas mixture comprises at least one anesthetic and the patient is fully anesthetized. In a second type, the ventilator supports the patient's own respiratory activity. The patient's own respiratory activity is exerted by patient's respiratory muscles. The patient's own respiratory muscles cause the patient to draw in breathable air. Electrical signals generated in the patient's body stimulate the patient's own respiratory muscles. It is also possible that the patient's own respiratory muscles are stimulated externally by an appropriate device.

The invention relates to supportive artificial ventilation. An anesthetic may also be administered to the patient during this supportive artificial ventilation.

It is desired that the ventilation strokes that the ventilator performs during supportive artificial ventilation are well synchronized with the patient's own respiratory activity. Ideal synchronization occurs when a ventilation stroke begins precisely when the patient's own respiratory muscles begin or at least attempt a breath, and the ventilation stroke ends precisely when the patient's own respiratory muscles end the breath or the attempt of a breath. Ideally, the ventilator detects each breath the patient takes or attempts to take and responds to each breath with a ventilation stroke, but only delivers a ventilation stroke in response to a detected breath.

As a rule, ideal synchronization cannot be achieved in practice.

U.S. Pat. No. 9,392,964 B2 and WO 2013/071 404 A1 describe various asynchrony types between the patient's own respiratory activity and artificial ventilation. Various features are presented to detect such asynchronies and to modify the artificial ventilation by the ventilator if necessary.

SUMMARY

It is an object of the invention to provide a monitoring process and a monitoring device that monitors a ventilator during supportive artificial ventilation for how well the ventilation strokes are synchronized with the patient's own respiratory activity.

The task is solved by a monitoring process with the features of the invention, by a ventilation process with the features of the invention, by a computer program with the features of the invention, by a monitoring unit with the features of the invention and by a ventilation arrangement with the features of the invention. Advantageous embodiments are disclosed. Advantageous embodiments of a process according to the invention are, as far as useful, also advantageous embodiments of the computer program and of the monitoring unit according to the invention and of the ventilation arrangement according to the invention and vice versa.

The monitoring process according to the invention and the signal processing monitoring unit according to the invention are capable of monitoring a ventilator.

The monitored ventilator is capable of providing supportive artificial ventilation to a patient. In supportive artificial ventilation, the ventilator performs a sequence of ventilation strokes, and the patient makes a sequence of inspiratory efforts. Each ventilation stroke delivers a quantity of a gas mixture comprising oxygen to the patient. In one embodiment, this gas mixture includes an anesthetic such that the patient is partially or fully sedated but not fully anesthetized. It is also possible that the gas mixture is free of an anesthetic. The proportion of oxygen in the gas mixture may be higher than the proportion in breathing air.

The patient's respiratory muscles perform their own respiratory activity while the patient is being artificially ventilated by the ventilator. The patient's own respiratory activity includes in particular his/her spontaneous breathing, which is triggered by electrical impulses generated in the patient's body. The patient's respiratory muscles may also be stimulated externally by a suitable device, for example by electrical signals or in a magnetic field. Spontaneous breathing and external stimulation can overlap.

Ideally, the patient's own respiratory activity will cause the patient to inhale and exhale breathing air or some other gas mixture with oxygen. However, it is possible that the patient tries to inhale but does not succeed in inhaling a relevant amount of the gas mixture. For example, the lungs are not elastic enough, and after an exhalation a relatively large amount of stale air still remains in the lungs. Therefore, the ventilator performs a sequence of ventilation strokes with the goal that each inspiratory effort of the patient triggers a breath, rather than just each inspiratory effort actually performed (each inspiratory activity). A single inspiratory effort is defined as an attempt by the patient to suck gas into the lungs. An inspiratory effort can succeed, i.e. lead to an inspiration event in which a relevant amount of gas flows into the patient's lungs, so that an inspiration event is a special case of an inspiratory effort. It can also remain an attempt. Ideally, therefore, both a completed and an attempted inspiration will result in one breath each.

The ventilator receives readings from a sensor arrangement comprising at least one respiratory sensor, optionally comprising a plurality of respiratory sensors. The respiratory sensor or at least one respiratory sensor whose readings are transmitted to the ventilator, preferably each connected respiratory sensor, is capable of each measuring an indicator that correlates with the patient's own inspiratory efforts. This respiratory sensor arrangement is thus able to detect not only an inhalation process during which a relevant amount of gas flows into the lungs, but also an inspiratory effort which does not lead to the inhalation of a relevant amount of gas. In particular, the measured indicator may be a pneumatic or electrical or mechanical or optical indicator. The sensor arrangement may be a component of the respiratory device. It is also possible that the or a respiratory sensor comprises a probe or transducer in or near the body of the patient.

The ventilator generates at least one respiratory signal (a respiratory signal). For generating this signal, the ventilator processes received readings from the or at least one respiratory sensor. The at least one respiratory signal (the generated respiratory signal or each generated respiratory signal) is an indicator for the patient's own respiratory activity. In particular, the respiratory signal correlates with the volume flow of gas to and optionally from the patient.

It is possible that the ventilator generates multiple respiratory signals, wherein each generated respiratory signal is an indicator for the patient's own respiratory activity, and wherein the ventilator preferably uses readings from different respiratory sensors to generate the different respiratory signals. Ideally, the respiratory signals match each other, but in practice they usually differ from each other.

Each inspiratory effort of the patient has a start and an end. The ventilator detects in the or at least one respiratory signal or in a combination of a plurality of respiratory signals the respective start and the respective end of each inspiratory effort, and thus in particular the start and the end of each completed inspiratory process. It is possible that the respiratory device detects a start and an end of the same inspiratory effort in several respiratory signals and detects a start and an end of this inspiratory effort from these detected values by aggregation.

The ventilator triggers the sequence of ventilation strokes with the goal that each patient inspiratory effort triggers exactly one ventilator breath and, conversely, each breath is triggered by exactly one inspiratory effort. Ideally, the start and end of the inspiratory effort coincide with the start and end of exactly one ventilation stroke, and the ventilation stroke is performed continuously throughout the inspiratory effort.

In practice, this ideal synchronization cannot usually be achieved. Rather, asynchronies occur.

In a preferred embodiment, the ventilator comprises a signal processing unit. This ventilator's signal processing unit generates the or at least one respiratory signal and triggers the sequence of ventilation strokes depending on the respiratory signal. In one embodiment, the monitoring unit according to the invention is a component of the ventilator. It is possible that the signal processing unit, which triggers the sequence of ventilation strokes, and the monitoring unit are implemented on the same signal processing device or on two different devices of the ventilator.

According to the invention, at least two possible asynchrony types are predetermined which may occur during the supportive artificial ventilation of the patient by the ventilator. Preferably, more than two different possible asynchrony types are predetermined. In each case, a criterion is predetermined as to when a predetermined asynchrony type has actually occurred. This criterion depends on the patient's own inspiratory efforts and on the sequence of ventilation strokes.

A predefined possible asynchrony type has actually occurred if the actual artificial ventilation deviates from an ideally synchronized artificial ventilation and one of the following events has occurred during the artificial ventilation:

The ventilation stroke begins or ends earlier than the triggering inspiratory effort.

The ventilation stroke starts or ends later than the triggering inspiratory effort.

A ventilation stroke is triggered without an inspiratory effort, i.e. the ventilation stroke is triggered incorrectly.

An inspiratory effort does not trigger a ventilation stroke, i.e. the inspiratory effort is not detected.

Two special cases for asynchrony types are that a ventilation stroke is mistakenly interrupted and then a new ventilation stroke is started while the patient is performing a single inspiratory effort, and a ventilation stroke is mistakenly continued while the patient completes an inspiratory effort and then begins a new inspiratory effort.

The monitoring unit is configured to automatically detect any occurrence of any predefined possible asynchrony type, i.e. to detect that an asynchrony has occurred and also to detect of which asynchrony type this asynchrony is. If the supportive artificial ventilation is ideally synchronized with the patient's own inspiratory efforts, then none of these possible asynchrony types actually occurs. However, in general ideally synchronized artificial ventilation cannot be achieved. The process according to the invention automatically detects each occurrence of a predetermined possible asynchrony type, at least if this asynchrony type occurs for longer than a predetermined time duration threshold. Of course it is possible that the same asynchrony type actually occurs several times, optionally with different durations.

According to the invention, the monitoring unit and the monitoring process determine for each predetermined possible asynchrony type a measure of how often and/or how long this asynchrony type actually occurred while the ventilator was performing the sequence of ventilation strokes, thus determining a measure for the frequency and/or a measure for the duration. It is possible to determine a measure for frequency and also a measure for duration.

According to the invention, a respective measure for frequency and/or duration is determined for each of at least two different asynchrony types. This feature allows for more targeted monitoring and adjustment of the ventilator than if it were merely determined in a blanket manner how often and/or how long ventilation strokes are not ideally synchronized with the patient's own respiratory activity. In particular, it is facilitated to adjust the ventilator to the requirements for ventilation of a particular patient. This adjustment can be performed manually or automatically.

According to the invention, the monitoring unit and the monitoring process detect an occurrence of a possible asynchrony type only if this occurrence lasts longer than the predetermined duration threshold. The duration threshold may be the same for all asynchrony types or may be different for at least two different asynchrony types. By considering the or each duration threshold, an asynchrony that only occurs for a very short time is not considered relevant and is therefore not considered. Such an occurrence of only a short duration is usually harmless to the patient. The duration threshold or each duration threshold for an asynchrony type may be fixed or may depend on a measured or estimated vital parameter of the patient, for example the patient's lung time constant, and/or on a parameter of artificial ventilation, for example the volume of a dead space in the fluid connection between the ventilator and the patient's lungs. In one embodiment the monitoring unit calculates the or at least one duration threshold depending on a value of a vital parameter of the patient.

The determined measure of how often and/or how long an asynchrony type has actually occurred can be used to better adapt the ventilator to the artificially ventilated patient's own breathing activity and thereby synchronize it with the patient's own inspiratory efforts. This is explained in more detail below.

In order to trigger the ventilation strokes synchronized with the patient's inspiratory efforts, it is necessary that the ventilator detects in the or at least one respiratory signal the respective start and the respective end of each inspiratory effort. Typically, the respiratory signal or each respiratory signal has an oscillatory pattern and correlates in particular with the volume flow from the ventilator to the patient and optionally back from the patient to the ventilator.

In order to detect the start and the end of an inspiratory effort in the or a respiratory signal, the ventilator typically applies a given decision rule that can be evaluated by a computer. This decision rule depends on at least one parameter, such as a lower bound on the amount or duration of volume flow. Knowing how often and/or for how long each of the predetermined possible asynchrony types has occurred makes it easier to assign an adjusted setpoint to the or each parameter for the decision rule and thereby to adapt the supportive artificial ventilation even better to the patient's own respiratory activity.

According to the embodiment, the monitoring unit calculates a target setpoint for the or a parameter of the decision rule. To calculate this target setpoint, the monitoring unit uses at least one determined measure for the frequency and/or duration of a predetermined possible asynchrony type. For example, the monitoring unit uses the or a determined measure for the asynchrony type that has actually occurred most frequently and/or for the longest duration in a predefined time period or span or since the start of supportive artificial ventilation. It is possible that the monitoring unit calculates the target setpoint depending on the respective measure for at least two asynchrony types.

The monitoring unit generates a message. In one embodiment, this message comprises information about the calculated target setpoint. In another embodiment, this message comprises information about a change in the currently used setpoint of the parameter. These two forms of implementation can be combined with each other.

In one embodiment, the monitoring unit causes the message to be transmitted to the ventilator. The ventilator uses this message to automatically adjust the setpoint of the decision rule parameter if necessary. In another embodiment, the monitoring unit causes the message to be output in a form that can be perceived by a human. The ventilator receives and evaluates a user input and changes the setpoint for the decision rule parameter based on the user input. This allows a user to verify whether or not a different setpoint should actually be assigned to the parameter, and to confirm or reject the proposed change. By assigning a different setpoint to the decision rule parameter depending on the message, it is achieved in many cases that at least one asynchrony type occurs less frequently and/or for a shorter period of time.

In many cases, the invention enables this adjustment of the supportive artificial ventilation to be performed more quickly and/or in a more targeted manner than with other possible approaches. This is because, according to the invention, the respective measure for duration and/or frequency is determined for at least two different possible asynchrony types. This enables a more targeted procedure than if only the general detection of how often and/or how long the ventilation strokes of the ventilator are not synchronized with the patient's own respiratory activity.

In some cases, a result of the monitoring unit can also be used to detect a failure of a respiration sensor. For example, the respiratory sensor is not positioned correctly or is defective. Or readings from that respiratory sensor are not correctly transmitted to the ventilator. Such a defect of a sensor often results in a certain asynchrony type occurring more frequently and/or for a longer period of time than with a correctly positioned and operating sensor. Thus, a measure for this asynchrony type determined in accordance with the invention may be indicative of an incorrectly positioned or defective respiratory sensor.

In one embodiment, a series of sampling time points is predetermined. For each predetermined sampling time, the monitoring unit determines which of the following four possible situations exists at that sampling time point:—

The patient performs an inspiratory effort. The ventilator performs a ventilation stroke.

The patient is not performing an inspiratory effort. The ventilator is not performing a ventilation stroke.

The patient is performing an inspiratory effort. The ventilator is not performing a ventilation stroke.

The ventilator performs a ventilation stroke. The patient does not perform an inspiratory effort.

At each sampling time point during supportive artificial ventilation, exactly one of the four possible situations is present. With ideally synchronized supportive artificial ventilation, only the first two situations occur at each sampling time. The last two situations are indicative of the occurrence of asynchrony.

To determine which of these four possible situations is actually present at a sampling time, the monitoring unit evaluates the or at least one respiratory signal and also determines when a ventilation stroke begins and when it ends. To determine when a respiratory stroke begins and when it ends, the monitoring unit preferably uses a signal from a controller of the ventilator and optionally at least one parameter of a fluid connection between the ventilator and the patient. It is also possible to continuously measure the volume flow in a fluid connection from the ventilator to the patient.

At each sampling time point, exactly one of the four possible situations mentioned above is detected. This results in a series of situations. The monitoring unit detects each situation sequence in this series of situations. A situation sequence to be detected has the following properties:

The series of situations comprises at least two immediately successive situations, preferably at least three immediately successive situations, particularly preferably exactly three immediately successive situations.

In each case, two immediately successive situations of the situation sequence differ from each other.

It is possible that a situation sequence is comprised of a first situation, a subsequent second situation and then again the first situation. A situation sequence can mean the occurrence of an asynchrony or an ideally synchronized ventilation stroke without asynchrony.

According to the invention, the monitoring unit determines for each predetermined possible asynchrony type a respective measure for the frequency and/or duration with which this asynchrony type has actually occurred. According to the embodiment just described, the monitoring unit determines for each predetermined possible asynchrony type which detected situations sequences means that this asynchrony type has actually occurred. Of course, it is possible that for at least one possible asynchrony type no matching situation sequence is detected, or that several matching situation sequences are detected that are spaced apart in time. To determine the measure for frequency and/or duration of a possible asynchrony type, the monitoring unit uses the matching situation sequences.

This embodiment makes it possible to quickly compare two different signals, namely the respiratory signal and a signal describing the sequence of ventilation strokes. By determining the four possible situations, this embodiment abstracts from quantitative parameters of artificial ventilation, in particular from the strength of a volume flow from the ventilator to the patient. This embodiment often increases the reliability and/or saves computing time and/or computing capacity.

In a variation of this embodiment, the monitoring unit determines for each possible asynchrony type how often matching situation sequences occur and/or how long the matching situation sequences last in total. Using this frequency and/or duration, the monitoring unit determines the measure for frequency and/or duration of the asynchrony type.

Each of the predefined possible asynchrony types describes a possible asynchrony between the patient's inspiratory efforts and the supportive artificial ventilation. Preferably, eight possible asynchrony types are predefined, namely four time asynchrony types and four event asynchrony types. For each of these eight predefined possible asynchrony types, a measure for frequency and/or duration is determined.

The following four possible asynchrony types are time asynchrony types, i.e. a ventilation stroke is triggered depending on an inspiratory effort, but too early or too late:

A ventilation stroke triggers an inspiratory effort (reverse triggering).
A ventilation stroke is triggered too late (late triggering).
A ventilation stroke is ended too late (late cycling off).
A ventilation stroke is ended too early (premature cycling off).

The remaining four possible asynchrony types are event asynchrony types, i.e. a ventilation stroke is falsely triggered (no inspiratory effort) or falsely not triggered (inspiratory effort not detected):

A ventilation stroke is triggered without an inspiratory effort (auto triggering).
An inspiratory effort does not trigger a ventilation stroke (missed effort).
A first inspiratory effort is completed during one breath and a second inspiratory effort is started during the same breath (missed expiration).
A first breath is completed during an inspiratory effort and a second breath is started during the same inspiratory effort (double triggering).

Preferably, at least one presentation is generated and output in a form perceptible by a human, for example visually on a display unit. The monitoring unit automatically generates the or each such presentation. Preferably, the presentation is continuously updated as the ventilator performs a sequence of ventilation strokes. The or at least one presentation refers, for example, to the entire history of artificial ventilation up to now, or to the history since the ventilator was last calibrated or changed, or since a parameter of the artificial ventilation was changed, or alternatively to a rolling period of time prior to the current time point. The or each generated presentation shows at a glance how often and/or how long at least two of the predetermined possible asynchrony types have actually occurred in each case. Preferably, the presentation is additionally provided with a textual description of each of the possible asynchrony types for which a measure is output.

This presentation allows a user to quickly grasp, virtually at a glance, how well the ventilation strokes are synchronized with the patient's inspiratory efforts. This effect is achieved in many cases even if the display surface of the display unit is relatively small and/or not optimally illuminated or is positioned angularly relative to a user. The presentation makes it easier for a user to assign a target setpoint to a parameter of the artificial ventilation wherein the target setpoint is more suitable for this patient than the currently used setpoint, if the synchronization is not sufficient.

In one embodiment, the monitoring unit generates both a measure for the respective frequency and a measure for the respective duration for at least two asynchrony types, preferably for each predetermined asynchrony type. Preferably, in the embodiment just described, both measures for the two asynchrony types are presented, for a total of at least four measures. In many cases, this presentation makes it even easier for a user to assess how well the ventilation strokes are synchronized with the patient's inspiratory efforts. In particular, based on the illustration showing the asynchrony types and the two measures per asynchrony type, a user can select between different possible remedies to obtain indications on how to improve synchronization or can improve the synchronization. In particular, a user may weight in the situation that one asynchrony type can be reduced by assigning a larger setpoint to a parameter and another asynchrony type by assigning a smaller setpoint to that parameter.

The following embodiment leads in many cases to a particularly clear presentation, even if the display unit on which the presentation is output is relatively small and/or poorly illuminated or oriented angularly to a user. According to this embodiment, for each presented asynchrony type two respective measures are determined, namely one for the frequency and one for the duration. The presentation is generated using two axes. These two axes are perpendicular or oblique to each other and are, for example, an x-axis and a y-axis. On one axis the determined measure for the frequency of an asynchrony type is plotted, for example the absolute number or the relative number in relation to the number of ventilation strokes. On the other axis, the determined measure for the duration of the asynchrony type is plotted, for example the absolute duration or the relative duration related to the total duration of artificial ventilation, in particular since the last setting or adjustment of the ventilator. In the plot, a two-dimensional area is shown for each asynchrony type. If the two axes are perpendicular to each other, this area has the shape of a rectangle. If they are at an angle to each other, this area has the shape of a trapezoid. The two dimensions of this area depend on the measure for frequency and the measure for duration, respectively. Preferably, the larger a dimension of the area is, the larger that dimension is.

This presentation shows a user even more intuitively which asynchrony types are currently relevant. Both a frequently occurring asynchrony type and a long-lasting asynchrony type result in a large area, and thanks to the embodiment just described a user can quickly grasp this.

The various forms of presentation just described thus lead to particularly ergonomic configurations for displaying information about the state and operation of the ventilator in a form that can be perceived by a human being.

Particularly preferably, two presentations are generated and continuously updated, and the display unit selectively displays one or the other presentation. For example, a user may switch between one presentation and the other presentation. One presentation shows how long and/or how often the four possible time asynchrony types occurred. The other presentation shows how long and/or how often the four possible event asynchrony types occurred. Preferably, each presentation comprises four quadrants, each quadrant representing one asynchrony type. In each quadrant an area is shown. At least one dimension of this area depends on the determined measures for this asynchrony type. It is also possible to output both presentations simultaneously. In this way, a user is quickly informed about the current state of the ventilator.

Furthermore, the invention relates to a computer program. This computer program is executable on a signal processing monitoring unit. This signal processing monitoring unit comprises a processor and a data memory. Preferably, the computer program can at least temporarily be stored in the data memory. The computer program is provided as a non-transitory computer-readable medium that is physical, transferable, and reproducible. The processor is adapted to execute the computer program.

A data connection with a ventilator can be or is established permanently or at least temporarily. This ventilator is able to perform supportive artificial ventilation for a patient, whereby the patient performs his/her own inspiratory efforts. The embodiment of such a ventilator has been described above. The data link allows data and/or signals to be transmitted from the ventilator to the monitoring unit, and optionally messages to be transmitted from the monitoring unit to the ventilator. In one embodiment, the monitoring unit is able to assign a setpoint to a parameter of the ventilator, and the ventilator uses this parameter setpoint to perform the supportive artificial ventilation. In one embodiment, the monitoring unit is adapted to control a display unit of the ventilator and to cause a presentation described above to be output on said display unit.

When a data link is established between the ventilator and the monitoring unit, preferably the processor of the monitoring unit executes the computer program, the monitoring unit causes a monitoring procedure according to the invention to be performed.

The invention further relates to a process of supportive artificial ventilation of a patient by a ventilator, wherein the ventilator performs a sequence of ventilation strokes with the aim that the ventilation strokes in the supportive artificial ventilation are ideally synchronized with the patient's own inspiratory efforts. A signal processing monitoring unit monitors how well the ventilation strokes are synchronized with the patient's own inspiratory efforts, and determines, for each predefined possible asynchrony type, a measure for how often and/or how long that asynchrony type actually occurred. This monitoring unit is configured according to the invention. Advantageous embodiments of the monitoring process according to the invention are also advantageous embodiments of the ventilation process.

The invention further relates to a ventilator arrangement. The ventilator arrangement comprises a ventilator, a sensor arrangement comprising at least one respiratory sensor and a monitoring unit according to the invention. The sensor arrangement (the respiratory sensor or each respiratory sensor) is capable of measuring an indicator (one or more indicators) that correlates with the patient's own inspiratory efforts. The ventilator is capable of providing supportive artificial ventilation to a patient and is configured as described above.

In the following, the invention is described with reference to example of embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
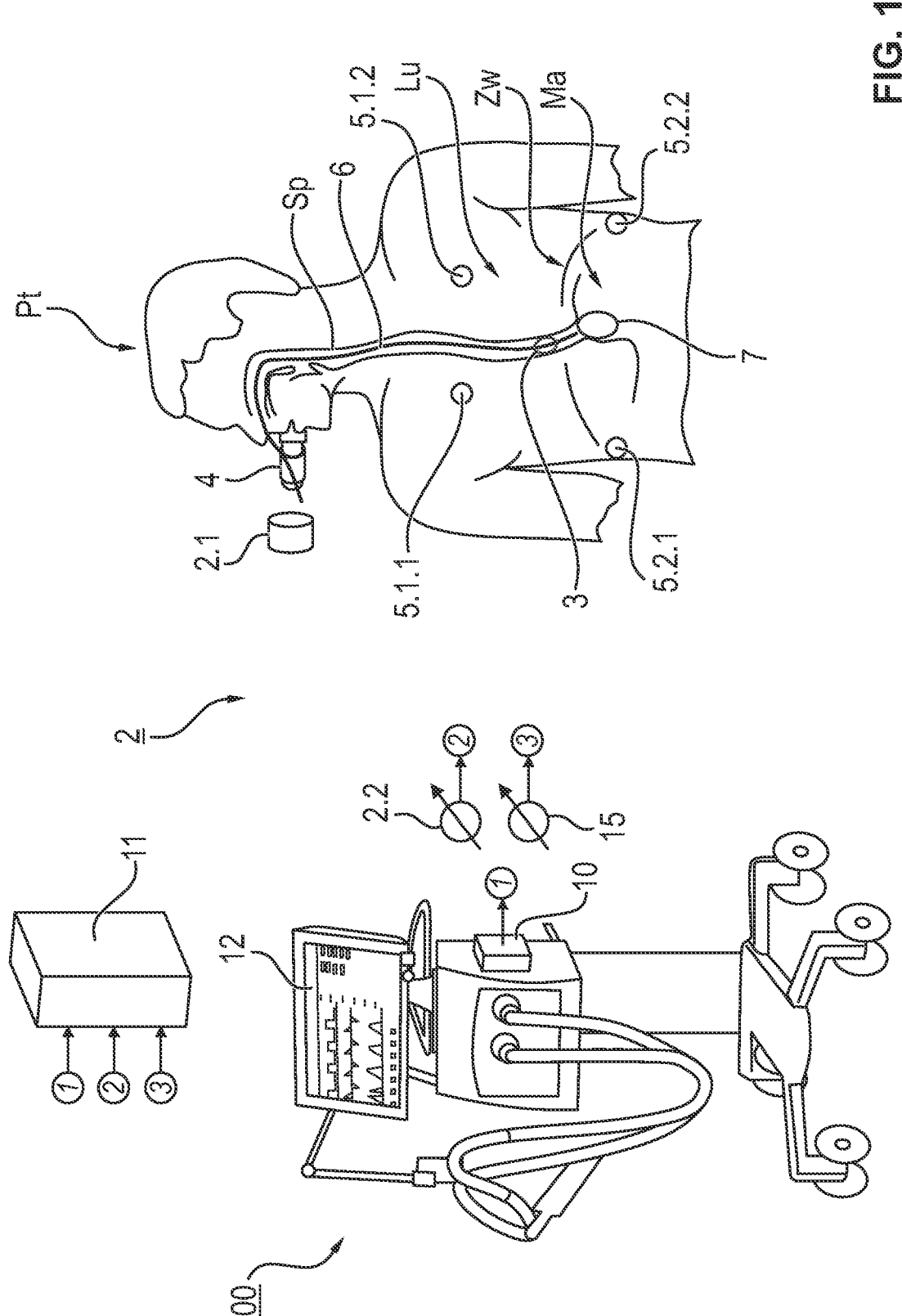
FIG. 1 is a schematic view showing an example with an artificially ventilated patient, a ventilator, and several sensors.

Referring to the drawings, in an embodiment, the invention is used to artificially ventilate a patient and thereby support the patient's own respiratory activity. The patient's own respiratory activity can be brought about by the patient's spontaneous breathing and/or by external stimulation of the patient's respiratory muscles.

A fluid connection is established between the patient's airway and a ventilator. Through this fluid connection, the ventilator supplies the patient with breathing air or another gas mixture containing oxygen. This gas mixture may comprise at least one anesthetic. In particular, when the patient is anesthetized, the fluid connection may be part of a ventilation circuit between the patient and the ventilator.

FIG. 1 shows an example of a patient Pt who is being artificially ventilated. The lungs Lu, the esophagus Sp, the stomach Ma and the diaphragm Zw of the patient Pt are shown schematically. In the mouth of the patient Pt, during artificial ventilation, there is a flexible connector 4 belonging to a patient-side coupling unit. In one embodiment, a flexible measurement catheter 6 is placed in the esophagus of the patient Pt, wherein the measurement catheter 6 starts in the connector 4. The patient-side coupling unit is at least temporarily attached in/or to the body of the patient Pt, and in an embodiment comprises the connector 4 and the measurement catheter 6.

A ventilator 100 with a display and control unit 12 and a signal processing unit 10 artificially ventilates the patient Pt. A fluid connection is established between the ventilator 100 and the patient-side coupling unit 4, 6. The ventilation tubing between the ventilator 100 and the patient Pt is not shown.

Various respiratory sensors measure various pneumatic or electrical or mechanical vital parameters of the patient Pt and/or parameters of the gas flow between the ventilator 100 and the lungs Lu of the patient Pt or of the gas delivered to the patient-side coupling unit 4, 6. To carry out the invention, not all of these respiratory sensors necessarily need to be present. The following respiratory sensors are shown as examples in FIG. 1:

A sensor 15 in or on the ventilator 100 measures an indicator of the volumetric flow, that is, the volume Vol' per unit time, of the flow of the gas mixture from the ventilator 100 to the patient Pt (for example, inspiratory volumetric flow or inspiratory minute volume) and/or back from the patient Pt to the ventilator 100 (for example, expiratory volumetric flow or expiratory minute volume).

An optional pneumatic sensor 2 comprises a transducer 2.1 having an aperture located near the patient's mouth Pt and tapping a sample of gas from the fluid connection. The tapped air is transmitted to a pressure sensor 2.2 via a tube not shown, and the pressure sensor 2.2 measures an indicator of airway pressure $P_{aw}$ (pressure in airway) in the fluid connection and optionally an indicator of volumetric flow Vol'. In one embodiment, the measurement sensor 2.1 is arranged in or on a Y-piece close to the connector 4, i.e. close to the mouth of the patient Pt. Preferably, the tapped gas sample is fed back into the fluid connection.

An optional probe 3 in the esophagus Sp of the patient Pt, preferably comprising a measuring balloon, measures an indicator of the time-varying pneumatic pressure $P_{es}$ (pressure in esophagus) in the esophagus Sp. The probe 3 is in fluid communication with the connector 4 via the measuring catheter 6 or is a component of the measuring catheter 6.

An optional further measuring balloon of probe 3 or an optional gastral probe 7 in the form of a measuring balloon placed in the stomach Ma measure an indicator for gastral pressure $P_{ga}$ in the stomach Ma.

Several measuring electrodes are attached to the chest of the patient Pt. FIG. 1 shows an example of a pair 5.1.1, 5.1.2 of measuring electrodes near the heart and a pair 5.2.1, 5.2.2 of measuring electrodes near the diaphragm. Using measured values of these optional measuring electrodes 5.1.1, . . . , 5.2.2 as well as a reference electrode for electrical ground, which is not shown, an electrocardiogram (ECG) and/or an electromyogram (EMG) of the patient Pt are generated, which are two different respiratory signals. It is possible that an ECG/EMG generated close to the heart is generated on the basis of measured values of the pair 5.1.1, 5.1.2 close to the heart and an ECG/EMG generated close to the diaphragm is generated on the basis of measured values of the pair 5.2.1, 5.2.2 close to the diaphragm.

The signal processing unit 10 is capable of automatically determining when air or another gas mixture flows into the respiratory system of the patient Pt and when a gas mixture flows out of the respiratory system again. Thus it is ideally capable of detecting each inspiration phase and each expiration phase of the patient Pt's own respiratory activity. For this purpose, the signal processing unit 10 uses measured values from at least one of the sensors 2, 3, 7 and 15 and optionally from the measuring electrodes 5.1.1 to 5.2.2.

The ventilator 100 performs a sequence of ventilation strokes. The signal processing unit 10 repeatedly automatically triggers the two steps of starting a ventilation stroke and ending it during the supportive artificial ventilation. The signal processing unit 10 controls a corresponding actuator (not shown) of the ventilator 100, for example a pump or at least one valve interacting with a blower. During each ventilation stroke, the ventilator 100 feeds breathing air or other gas mixture into the fluid connection, and this gas mixture flows to the patient Pt.

In the embodiment, the patient Pt's own respiratory muscles draw in a gas mixture, i.e. the patient Pt inhales a gas mixture from the fluid connection. The inhalation may be caused by the spontaneous breathing of the patient Pt. Optionally, the patient's respiratory muscles are externally stimulated. The ventilator 100 assists the patient Pt's own breathing activity by the ventilator 100 delivering a gas mixture to the lungs Lu, said gas mixture comprising oxygen.

In the following, a distinction is made between the terms "inhalation process" and "inspiratory effort" of patient Pt. The patient's own respiratory musculature Pt, which is stimulated in the patient Pt's body itself and/or externally stimulated, attempts to suck in a gas. This attempt is called an inspiratory effort. If this attempt succeeds, i.e. a relevant amount of the aspirated gas actually flows into the lungs Lu, then the patient Pt has actually taken a breath and therefore also performed an inhalation process. However, it is also possible that an inspiratory effort does not cause an inhalation event that results in a measurable/relevant volume flow into the airway of the patient Pt. In particular, this situation may occur when the lungs Lu of the patient Pt are not very elastic and therefore a relatively large amount of used air remains in the lungs Lu after an exhalation event, leaving little room for new gas. Furthermore, in some situations, the ventilator 100 performs an occlusion. During an occlusion, the patient Pt is briefly prevented from actually breathing in. During such an occlusion, in many cases a lung mechanical parameter of the patient Pt can be better measured than in a situation where gas flows into the lungs Lu of the patient Pt.

Ideally, any inspiratory effort performed by the patient Pt with the patient's own respiratory muscles immediately triggers a ventilation stroke of the ventilator 100, in one embodiment except during an occlusion. Ideally, this ventilation stroke is immediately terminated when the patient Pt ceases the inspiratory effort. Thus, each inspiratory effort of the patient Pt ideally triggers exactly one ventilation stroke of the ventilator 100, and each ventilation stroke is triggered by exactly one inspiratory effort. The ventilation strokes of the ventilator 100 are thus ideally fully synchronized with the patient Pt's own respiratory activity.

The patient's own respiratory muscles Pt perform breaths in which air or another gas mixture first flows into the lungs (inspiration) and then flows out of the lungs again (expiration). In the following, the term "inspiration" is also used for an inspiratory effort that does not result in a measurable breath and thus does not result in a measurable inhalation process.

The respiratory sensors described above are each capable of providing measured values. From measured values from at least one respiratory sensor, the signal processing unit 10 generates a signal that correlates with the patient Pt's own respiratory activity. This signal is referred to as a "respiratory signal" and is denoted by $Sig_{res}$. Typically, readings from different respiratory sensors will result in different respiratory signals. Typically, the actual respiratory activity of patient Pt differs at least some of the time from the respiratory signal or each respiratory signal $Sig_{res}$ obtained, such that the respiratory signal or each respiratory signal $Sig_{res}$ is only an approximation of patient Pt's own actual respiratory activity.

In one embodiment, the signal processing unit 10 detects, by evaluating at least one respiratory signal $Sig_{res}$, that the patient Pt's own respiratory muscles have started an inhalation process or at least an inspiratory effort (start of an inspiration phase). The readings leading to this respiratory signal $Sig_{res}$ come from the or at least one pneumatic respiratory sensor, for example the pneumatic sensor 2 in front of the patient Pt's mouth, the probe 3 in the patient Pt's esophagus Sp or the gastral probe 7 in the patient Pt's stomach. The readings from these pneumatic respiratory sensors each result in a pneumatically obtained respiratory signal $Sig_{res}$.

In a preferred embodiment, at least one pneumatic respiratory signal $Sig_{res}$ is used which correlates with the patient's inspiratory efforts Pt and not only with the breaths actually taken. The pneumatic respiratory sensors 15, 3 and 7 are capable of providing measured values from which such a respiratory signal $Sig_{res}$ is generated. The respiratory signal $Sig_{res}$, which is generated from the measured values of the pneumatic respiration sensor 2, on the other hand, correlates with the breaths actually taken by the patient Pt.

In another embodiment, the fact that the patient Pt's own respiratory muscles are stimulated to move by a sequence of electrical pulses generated in the patient Pt's body and/or optionally by a stimulating device is exploited. These electrical impulses can be measured and result in an electrical signal. This electrical signal for the respiratory muscles correlating with the internal and/or external stimulation is referred to as an "electrical respiratory signal" and can be measured approximately. The cardiac activity of the patient Pt is triggered by another sequence of electrical signals generated in the body of the patient Pt. From this sequence, a signal for cardiac activity can be generated, which is referred to as a "cardiogenic signal".

For the measured values of the measuring electrodes 5.1.1 to 5.2.2 as well as the measured values of the reference electrode not shown, a signal preprocessing is carried out in one embodiment, which preferably comprises a summation and a smoothing of the measured electrical measured values and provides a so-called envelope. This envelope is or provides a sum signal $Sig_{Sum}$, which results from a superposition of the electrical respiratory signal with the cardiogenic signal and may be influenced by interfering signals. Interfering signals can come from the patient Pt's body and from the environment. The influence of the cardiogenic signal on the sum signal $Sig_{Sum}$ is at least approximately compensated by calculation. For example, in the sum signal $Sig_{Sum}$ those sections are detected which originate from one heartbeat each, for example one so-called QRS section each. Or a standardized course of the cardiogenic signal in the course of a single heartbeat is subtracted from the sum signal, a so-called ECG template. The computational compensation provides an approximation for the electrical respiratory signal $Sig_{res}$. The estimate for the electrical respiratory signal $Sig_{res}$ obtained in this way also indicates when the patient Pt begins an inspiratory effort and when the patient Pt ends it.

It is possible that a first electrical respiratory signal $Sig_{res}$ is obtained from measured values of the pair 5.1.1, 5.1.2 near the heart and a second electrical respiratory signal is obtained from measured values of the pair 5.2.1, 5.2.2 near the diaphragm. As a rule, these two electrical signals differ from each other.

Figures 2A, 2B:
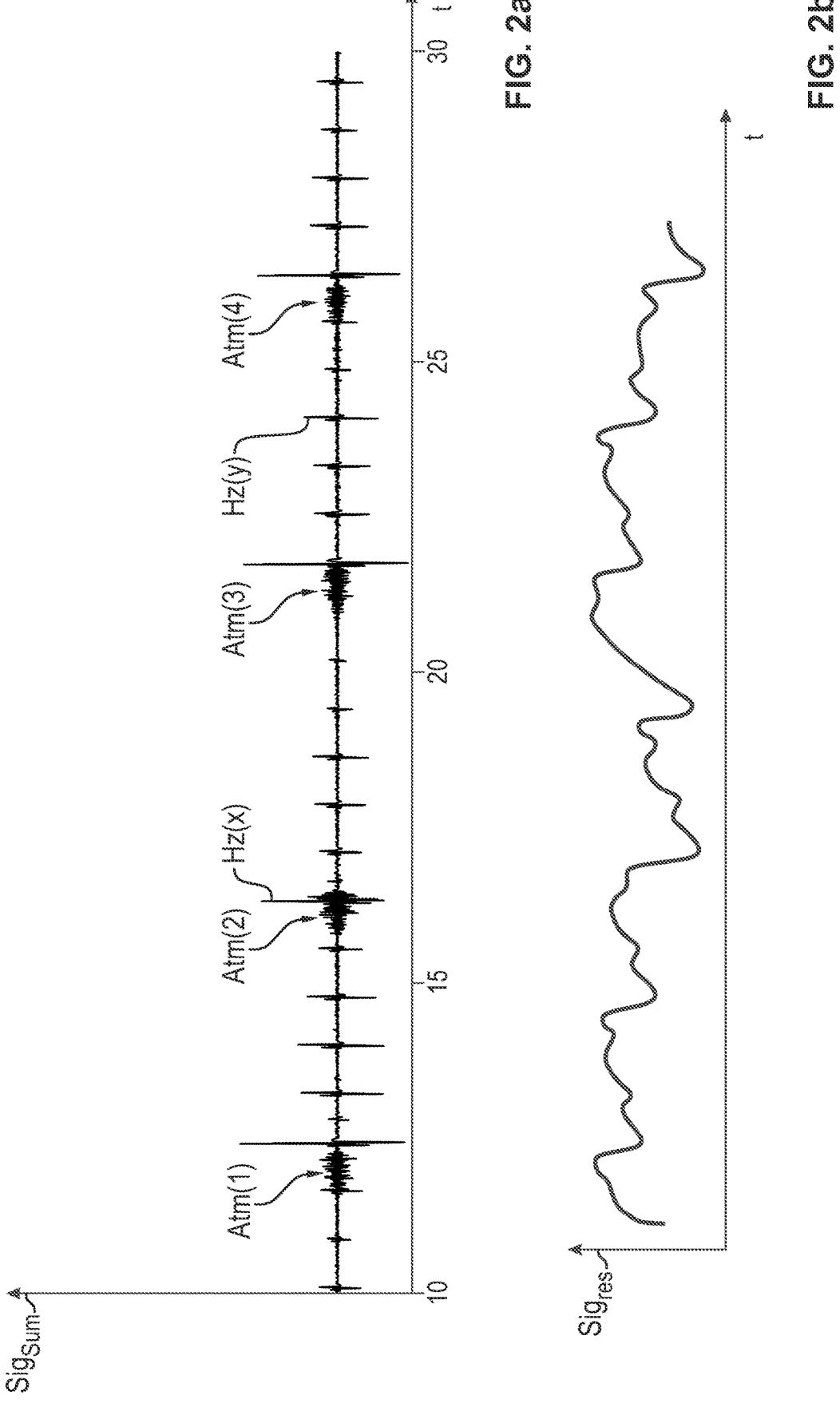
FIG. 2a is a view of an example of an electrical sum signal obtained by measurements.
FIG. 2b is a view of an example of a pneumatic respiratory signal obtained by measurements.

FIG. 2a shows an example of an electrical sum signal $Sig_{Sum}$, which was obtained from measured values of the two pairs 5.1.1, 5.1.2 and 5.2.1, 5.2.2 of measuring electrodes as well as measured values of the non-generated reference electrode. On the x-axis the time t is plotted, on the y-axis the respective value of the sum signal $Sig_{Sum}$. The respective effect of a sequence of heartbeats, e.g. the heartbeats Hz(x) and Hz(y), and a sequence of breaths, e.g. the breaths Atm(1), . . . , Atm(4), can be seen. From this electrical sum signal $Sig_{Sum}$ an electrical respiratory signal $Sig_{res}$ can be generated, preferably by compensating the influence of the cardiogenic signal on the sum signal $Sig_{Sum}$ by calculation. FIG. 2b shows an exemplary pneumatic respiratory signal $Sig_{res}$, which was generated by evaluating measured values from one of the sensors 3, 7, 15.

In a further embodiment not shown, readings from a mechano-myographic sensor provide a mechanical respiratory signal that correlates with the activity of the patient's own respiratory muscles Pt.

The signal processing unit 10 detects in at least one respiratory signal $Sig_{res}$ the respective start and the respective end of each inspiratory effort. The embodiments just described for generating respiratory signals in different ways can be combined with each other. In one embodiment, at least two different respiratory signals are present. These respiratory signals ideally match, but in practice generally differ from each other and from the actual inspiratory efforts. In one embodiment, the signal processing unit 10 generates an averaged respiratory signal $Sig_{res}$ from a plurality of respiratory signals and uses this averaged respiratory signal $Sig_{res}$, to detect the patient Pt's inspiratory efforts. On the other hand, in another embodiment, the signal processing unit 10 uses a plurality of respiratory signals to detect the inspiratory efforts of the patient Pt.

Ideally, each inspiratory effort or at least each inhalation event of the patient Pt is visible in the or each respiratory signal $Sig_{res}$, furthermore each exhalation event. Ideally, the signal processing unit 10 detects each inspiratory effort in each respiratory signal $Sig_{res}$ and always detects those times at which the inspiratory effort starts or ends. Ideally, the respiratory strokes of the ventilator 100 are synchronized with the inspiratory efforts of the patient Pt.

In practice, an inspiratory effort may not be detected at all in the or at least one respiratory signal $Sig_{res}$. Furthermore, it is possible that the signal processing unit 10 detects the same inspiratory effort of the patient Pt in multiple respiratory signals $Sig_{res}$, but with different times for the start and/or for the end of the inhalation. The different estimates may be combined at the wrong time or even misclassified as two different inspiratory efforts. It is also possible that the signal processing unit 10 in the respiratory signal or a respiratory signal $Sig_{res}$ supposedly detects an inspiratory effort, although the patient Pt has not performed an inspiratory effort at that time. Indeed, the respiratory signal or each respiratory signal $Sig_{res}$ inevitably deviates from the patient Pt's own actual respiratory effort. Some reasons for this are: a distance occurs between the diaphragm Zw and other regions of the patient Pt's body that cause the inspiratory efforts and the measurement point at which the measurement values for a respiratory signal $Sig_{res}$ are measured, whereby interfering signals may become effective. In addition, measurement inaccuracies and measurement errors of the sensors used usually occur, and further signals generated in the patient Pt's body or even outside may affect the respiratory signal $Sig_{res}$ obtained. It is also possible that the signal processing unit 10 does not detect an inspiratory effort of the patient Pt at all.

Preferably, the signal processing unit 10 detects an inspiratory effort of the patient Pt when this inspiratory effort becomes visible in the respiratory signal or at least one respiratory signal $Sig_{res}$, even when this inspiratory effort does not become visible in another respiratory signal $Sig_{res}$. If the same inspiratory effort is visible in several respiratory signals, the signal processing unit 10 preferably detects in at least two of these respiratory signals the respective time for the start and the end of the inhalation. If multiple respiratory signals are present, in one embodiment the signal processing unit 10 averages over the detected times for the start of the inspiratory effort and averages over the detected times for the end of the inspiratory effort, thereby determining an averaged start time and an averaged end time for each inspiratory effort. In this averaging, weight factors are taken into account in one embodiment, where a weight factor is greater the more reliable a particular respiratory sensor and/or the more reliable the derivation of the respiratory signal from that sensor. It is also possible that the time points in the respiratory signal that currently has the highest reliability are used.

As a rule, a period of time elapses between the time at which the patient Pt begins or ends an inspiratory effort and the time at which this event is detected in a pneumatic respiratory signal $Sig_{res}$, in particular if the pneumatic respiratory sensor used is located outside the body of the patient Pt. One reason is that the inspiratory effort must have resulted in a sufficiently large volume flow at the respective measuring point of a pneumatic respiratory sensor before the inspiratory effort is detected in the respiratory signal $Sig_{res}$ from this respiratory sensor. Moreover, time also elapses between the time when the patient Pt's body or even a stimulating device generates electrical impulses which activate the patient's own respiratory muscles and which are measured, and the time when the patient's own respiratory muscles actually begin an inspiratory effort. This time span may depend on the so-called neuromuscular efficiency of the patient's own respiratory musculature, i.e. how quickly and how well the patient's own respiratory musculature Pt responds to stimulating electrical impulses. These two time spans can be estimated in many cases, but any estimate may be subject to uncertainty.

The patient's actual own respiratory activity and therefore the respiratory signal or each respiratory signal $Sig_{res}$ generally oscillate, and generally the amplitude and frequency of this oscillation varies over time. The signal processing unit 10 of the ventilator 100 automatically applies a decision rule to the or each respiratory signal $Sig_{res}$ obtained to detect in the respiratory signal $Sig_{res}$ the start and end of an inspiratory effort of the patient Pt, and to start and end a ventilation stroke depending on the detected start and end of the detected inspiratory effort. This decision rule applies parameters in many cases, for example the following operating parameters:

If a measure for the volume flow of respiratory air to the lungs Lu of the patient Pt is greater than a predetermined barrier x, optionally greater than the barrier x within a predetermined time period T, it is decided that the patient Pt has started an inspiratory effort, and a new ventilation stroke is started.

If the measure for this volume flow becomes less than a percentage y of the last measured maximum volume flow, i.e. the maximum volume flow at this inspiratory effort, it is decided that the patient Pt has completed the inspiratory effort, and the current ventilation stroke is terminated.

Setpoints for these operating parameters x, y are determined on the basis of the following conflicting requirements:

Every inspiratory effort should be detected.

The start and end of each inspiratory effort that the patient Pt actually performs should be detected as accurately as possible.

During supportive ventilation, a ventilation stroke should only be performed if patient Pt is also making an effort to breathe in. It should be avoided that a ventilation stroke is erroneously executed due to a supposed inspiratory effort, although the patient Pt is not inhaling. In particular, it is generally intended to avoid the ventilator 100 performing a ventilation stroke while the patient Pt is exhaling.

Figure 3:
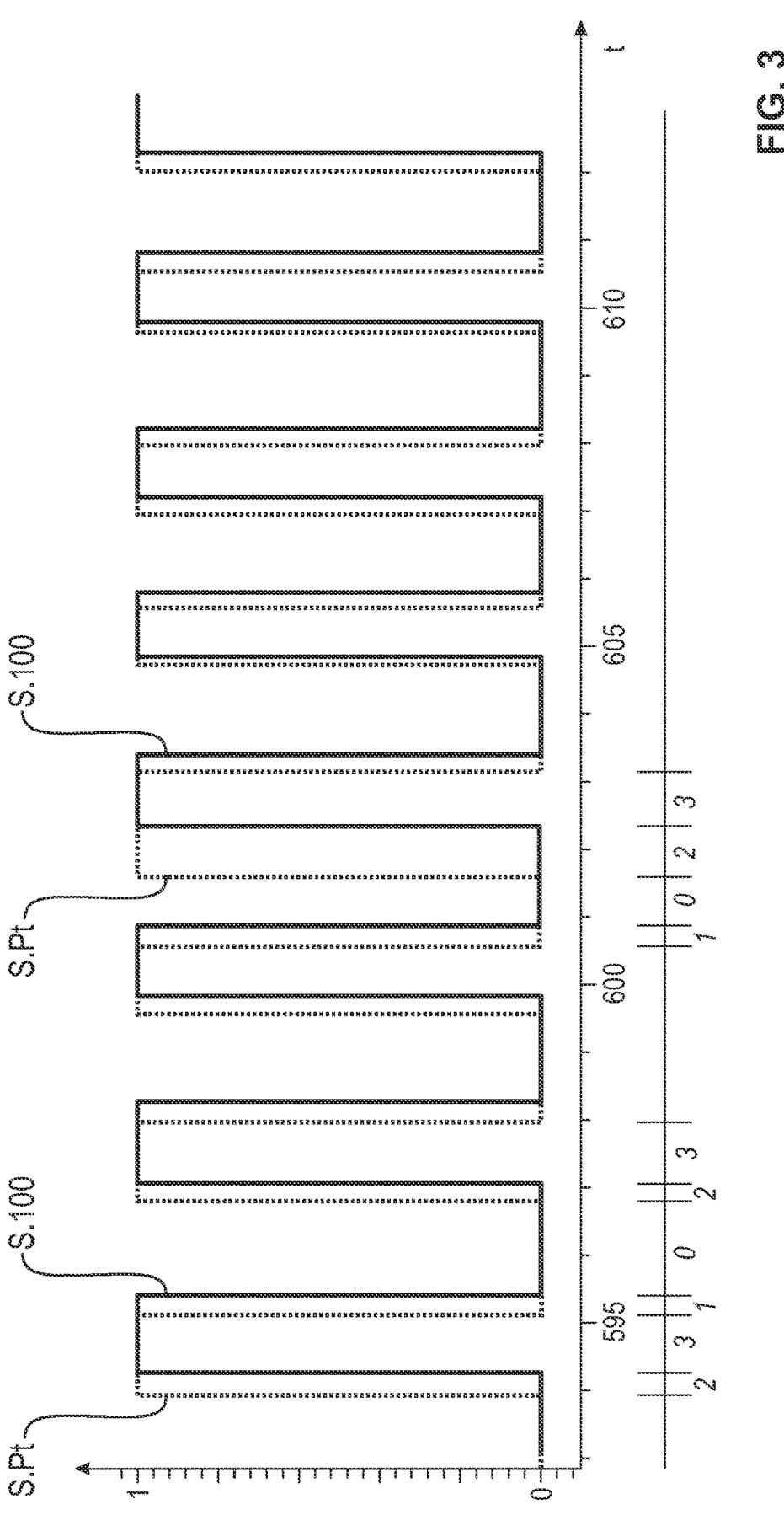
FIG. 3 is a schematic view showing an exemplary course for a sequence of breaths of the patient and a sequence of ventilation strokes of the ventilator.

FIG. 3 illustrates by means of an exemplary schematic diagram a situation in which the ventilation strokes of the ventilator 100 "lag behind" the patient's own respiratory activity Pt. The time in [sec] is plotted on the x-axis. Time periods in which the patient Pt's own respiratory musculature causes an inspiratory effort, i.e. attempts to suck in air, are coded with a 1 in the course S.Pt (shown dashed), the other time periods with a 0. Correspondingly, time periods in which the ventilator 100 delivers breathing air to the patient Pt, i.e. executes a ventilation stroke, are coded with a 1 in the course S.100 (shown solid), the other time periods with a 0.

In the example shown, the ventilation strokes are started and ended depending on a pneumatic respiratory signal $Sig_{res}$, i.e. depending on readings from at least one pneumatic sensor 15, 3, 7. In the example shown, each ventilation stroke starts and ends later than the inspiratory effort that triggers that ventilation stroke. Various possible reasons for the supportive artificial ventilation "lagging behind" the patient's own respiratory activity have already been mentioned above.

It is also possible that a ventilation stroke begins earlier than the inspiratory effort that triggers that ventilation stroke. In particular, this situation may occur if the ventilation stroke is triggered by an estimate for an electrical respiratory signal $Sig_{res}$, where this electrical signal $Sig_{res}$ is generated depending on electrical pulses generated in the patient Pt's body and not by the start of an executed inspiratory effort. One possible cause of a ventilation stroke starting too early is the following: a threshold to detect an electrical respiratory signal $Sig_{res}$ for a patient Pt inspiratory effort is set too low, i.e., the sensor is too sensitive. Possible reasons for supportive artificial ventilation to precede the patient's own respiratory effort have also been mentioned above.

At each sampling time, the following four situations may occur, which in a preferred embodiment are encoded with four different values. The following table 1 shows these four situations and exemplary their respective coding.

TABLE 1

| Coding | Ventilation stroke performed (air flows from ventilator 100 to patient Pt)? | Inspiratory effort performed (own respiratory muscles trying to draw in breath)? |
|---|---|---|
| 0 | No | No |
| 1 | Yes | No |
| 2 | No | Yes |
| 3 | Yes | Yes |

Of course, other codings than the digits 0, 1, 2, 3 are also possible.

In the following, the designations "Situation 0" to "Situation 3" are used as abbreviations. These codings are entered as an example under the x-axis in FIG. 3.

In the following, a sequence of three situations is referred to as a "sequence", provided that two situations immediately following each other are different from each other.

If the ventilator 100 is ideally synchronized with the patient Pt's own respiratory activity, only situations 0 and 3 occur. An ideally synchronized ventilation stroke leads to the situation sequence [0, 3, 0]. In practice, situations 1 and 2 usually occur as well. These situations mean asynchrony.

As a rule, it is completely harmless for the patient Pt if the start and end of a ventilation stroke does not deviate from the start and end of the inspiratory effort that triggers this ventilation stroke by more than a predefined duration limit. This duration limit may be fixed for all patients Pt and all situations and may be, for example, 100 msec. The duration limit may also depend on measured vital parameters of the patient Pt and/or on the way in which the ventilation strokes differ from the inspiratory efforts. Therefore, in the following, a situation 1 or 2 is only registered if this situation 1 or 2 lasts longer than the predetermined duration limit. This can be ensured, for example, with a sufficiently large sampling frequency or with signal preprocessing.

Figure 4:
FIG. 4 is a schematic view showing a time course of four different situations during supportive ventilation.

Situations 1 and 2 are referred to as "asynchrony situations". FIG. 4 shows the time course of the four situations 0, 1, 2, 3 for the course of FIG. 3. In addition, FIG. 3 shows some exemplary time periods in which one of these four situations occurs. On the x-axis of FIG. 4 again the time tin [sec] is plotted, on the y-axis the value 0, 1, 2, 3 for the respective situation.

A sequence of sampling time points is predefined. For each sampling time point it is automatically determined which of the four possible situations 0, 1, 2, 3 is present at this sampling time point. This procedure provides a sequence of situations. As explained earlier, a section of the situations sequence consisting of three situations in immediate succession is called a "sequence", provided that two situations in immediate succession are different from each other. Examples of situation sequences are [0,1,0], [2,3,0] and [1,0, 3]. With n=4 different possible situations there are $$n*(n-1)*(n-1)=36$$

various possible situation sequences.

An "asynchrony sequence" is defined as a situation sequence in which the situation in the middle is an asynchrony situation, i.e. equal to 1 or equal to 2. The invention makes it possible to selectively detect the asynchrony sequences during supportive artificial ventilation of the patient Pt. With n=4 different possible situations and m=2 asynchrony situations, there are $$(n-1)*m*(n-1)=18$$

various possible asynchrony sequences.

The following Table 2 shows by way of example which of these 18 possible asynchrony sequences have which technical meanings.

TABLE 2

| Sequence | technical importance |
|---|---|
| [0, 1, 0] | Ventilation stroke performed without a temporally overlapping inspiratory effort |
| [0, 1, 2] | First neither ventilation stroke nor inspiratory effort, then only ventilation stroke performed, then only inspiratory effort performed |
| [0, 1, 3] | Ventilation stroke started before inspiratory effort |
| [0, 2, 0] | Inspiratory effort performed without a temporally overlapping ventilation stroke |
| [0, 2, 1] | First only inspiratory effort, immediately afterwards only ventilation stroke performed |
| [0, 2, 3] | Inspiratory effort started before ventilation stroke |
| [1, 2, 0] | Ventilation stroke terminated before inspiratory effort |
| [1, 2, 1] | Inspiratory effort started and ended during a ventilation stroke |
| [1, 2, 3] | Ventilation stroke started before inspiratory effort |
| [2, 1, 0] | Inspiratory effort terminated before ventilation stroke |
| [2, 1, 2] | Ventilation stroke started and ended during inspiratory effort |

18

TABLE 2-continued

| Sequence | technical importance |
|---|---|
| [2, 1, 3] | Inspiratory effort started before ventilation stroke |
| [3, 1, 0] | Inspiratory effort terminated before ventilation stroke |
| [3, 1, 2] | First inspiratory effort finished before ventilation stroke, then second inspiratory effort started without ventilation stroke |
| [3, 1, 3] | First inspiratory effort completed during one breath and second inspiratory effort started during the same breath. |
| [3, 2, 0] | Ventilation stroke terminated before inspiratory effort |
| [3, 2, 1] | First ventilation stroke completed before inspiratory effort, second ventilation stroke started without inspiratory effort. |
| [3, 2, 3] | First ventilation stroke completed during an inspiratory effort and second ventilation stroke started during the same inspiratory effort. |

Table 3 below shows the clinical meanings for eight relatively common asynchrony type sequences. These eight asynchrony type sequences function as eight possible asynchrony types within the meaning of the claims.

TABLE 3

| Sequence | clinical significance (details) | clinical significance (terms) |
|---|---|---|
| [0, 1, 0] | Ventilation stroke triggered by itself | Auto Triggering |
| [0, 1, 3] | Ventilation stroke triggers inspiratory effort | Reverse Triggering |
| [0, 2, 0] | Inspiratory effort missed | Missed Effort |
| [0, 2, 3] | Ventilation stroke triggered too late | Late Triggering |
| [3, 1, 0] | Ventilation stroke ended too late | Late Cycling Off |
| [3, 1, 3] | End of an inspiratory effort missed (exhalation missed) | Missed Expiration |
| [3, 2, 0] | Ventilation stroke ended too early | Premature Cycling Off |
| [3, 2, 3] | new ventilation stroke triggered during inspiratory effort | Double Triggering |

Two classes of asynchrony sequences can be distinguished, namely time asynchronies and event asynchronies (desynchronies). In a time asynchrony, the ventilation stroke starts later or earlier than the inspiratory effort that triggers this ventilation stroke. If only time asynchronies occur during supportive artificial ventilation, each inspiratory effort of the patient Pt triggers exactly one ventilation stroke of the ventilator 100. In an event asynchrony, an inspiratory effort does not trigger a ventilation stroke at all, or a ventilation stroke is triggered without an inspiratory effort. Or, an inspiratory effort by the patient Pt is supported by a ventilation stroke, but the patient interrupts the inspiratory effort, or the ventilator 100 interrupts the supporting ventilation stroke. The four relatively frequent asynchrony sequences [0,1,3], [0,2,3], [3,2,0], and [3,1,0] are time asynchronies, and the remaining four relatively frequent asynchrony sequences [0,2,0], [3,1,3], [0,1,0], and [3,2,3] are event asynchronies.

A signal processing monitoring unit 11, which monitors the supportive artificial ventilation by the ventilator 100 and which comprises a processor and a data memory, receives the generated respiratory signal $Sig_{res}$, optionally each individual respiratory signal $Sig_{res}$ from different respiratory sensors, and detects in the or each respiratory signal $Sig_{res}$ obtained the inspiratory efforts of the patient Pt and for each inspiratory effort its respective start and its end. Because this monitoring unit 11 monitors the ventilator 100 but does not itself initiate any ventilation stroke, the monitoring unit 11 can evaluate a longer section of the or each respiratory signal $Sig_{res}$. For this evaluation, the monitoring unit 11 has a greater computing time available than is available to the signal processing unit 10 to trigger ventilation strokes. The monitoring unit 11 may be a component of the ventilator 100 or may be arranged outside the ventilator 100. However, it is also possible that the same signal processing device performs both the functions of the signal processing unit 10 and the functions of the monitoring unit 11.

In one embodiment, the monitoring unit 11 applies a learning method to each temporally last portion of the respiratory signal $Sig_{res}$ to detect the start and the end of an inspiratory effort. In one embodiment, the learning method is applied to the N temporally last detected inspiratory efforts, where N is a predetermined number. In another embodiment, the learning method is applied to the temporally most recent portion of the respiratory signal $Sig_{res}$, where this most recent portion has a predetermined time duration T. In many cases, the application of a learning method increases the reliability with which the respective start and the respective end of the inspiratory efforts are detected in the respiratory signal $Sig_{res}$.

In addition, for each ventilation stroke, the monitoring unit 11 receives from the signal processing unit 10 an identification of those two times at which this ventilation stroke was started and ended, respectively.

The monitoring unit 11 compares the respiratory signal $Sig_{res}$, received or generated by averaging or by any other suitable type of signal processing, which correlates with the patient Pt's own respiratory activity, with the time course of the ventilation strokes performed by the ventilator 100, exemplified by the curve S.100 shown in FIG. 3. By comparing the two curves, the monitoring unit 11 detects any possible asynchrony sequence, exemplarily shown in Table 3. Preferably, an asynchrony situation 1 or 2 is only taken into account here if it lasts longer than the predefined time duration limit of, for example, 100 msec or of variable duration. The monitoring unit 11 generates a temporal sequence n1 n2 n3 . . . , where n1, n2, n3 are codes for the possible situations, in this case a number 0, 1, 2 or 3 respectively. This series is hereinafter referred to as the "series of situations".

Preferably, the monitoring unit 11 automatically counts how often in the series of situations which asynchrony sequence occurs. In some cases, a certain asynchrony sequence is only relevant if its frequency in the series of sequences is above a predetermined frequency limit or follows a certain occurrence pattern in the series of situations. This applies in particular to the asynchrony sequence [0,1,3] (reverse triggering), i.e. a ventilatory effort triggers an inspiratory effort instead of an inspiratory effort triggering a ventilatory effort.

As has been explained, the signal processing unit 10 applies a decision rule to detect in the respiratory signal $Sig_{res}$ the respective start and the respective end of each inspiratory effort. This decision rule depends on at least one parameter. In one embodiment, the monitoring unit 11 automatically assigns a setpoint to this parameter or modifies an already assigned setpoint, depending on how often and/or how long a possible asynchrony sequence has actually occurred. For example, if individual inspiratory efforts are not detected, a lower bound for the volume flow in the decision rule is preferably lowered. Conversely, if individual ventilation strokes are triggered without a corresponding inspiratory effort, this lower volume flow barrier is raised.

In the embodiment example, the monitoring unit 11 causes the result of the monitoring to be output on the display and control unit 12. In many cases, at least one of the boundary conditions that frequently occur in everyday clinical practice is to be observed, namely that the display and control unit 12 is relatively small, nevertheless relatively much information must or should be output, sometimes there is no optimal lighting and a user should be able to quickly grasp the presented results, even under high stress and/or stimulus overload, both of which often occur in everyday clinical practice.

Figure 5:
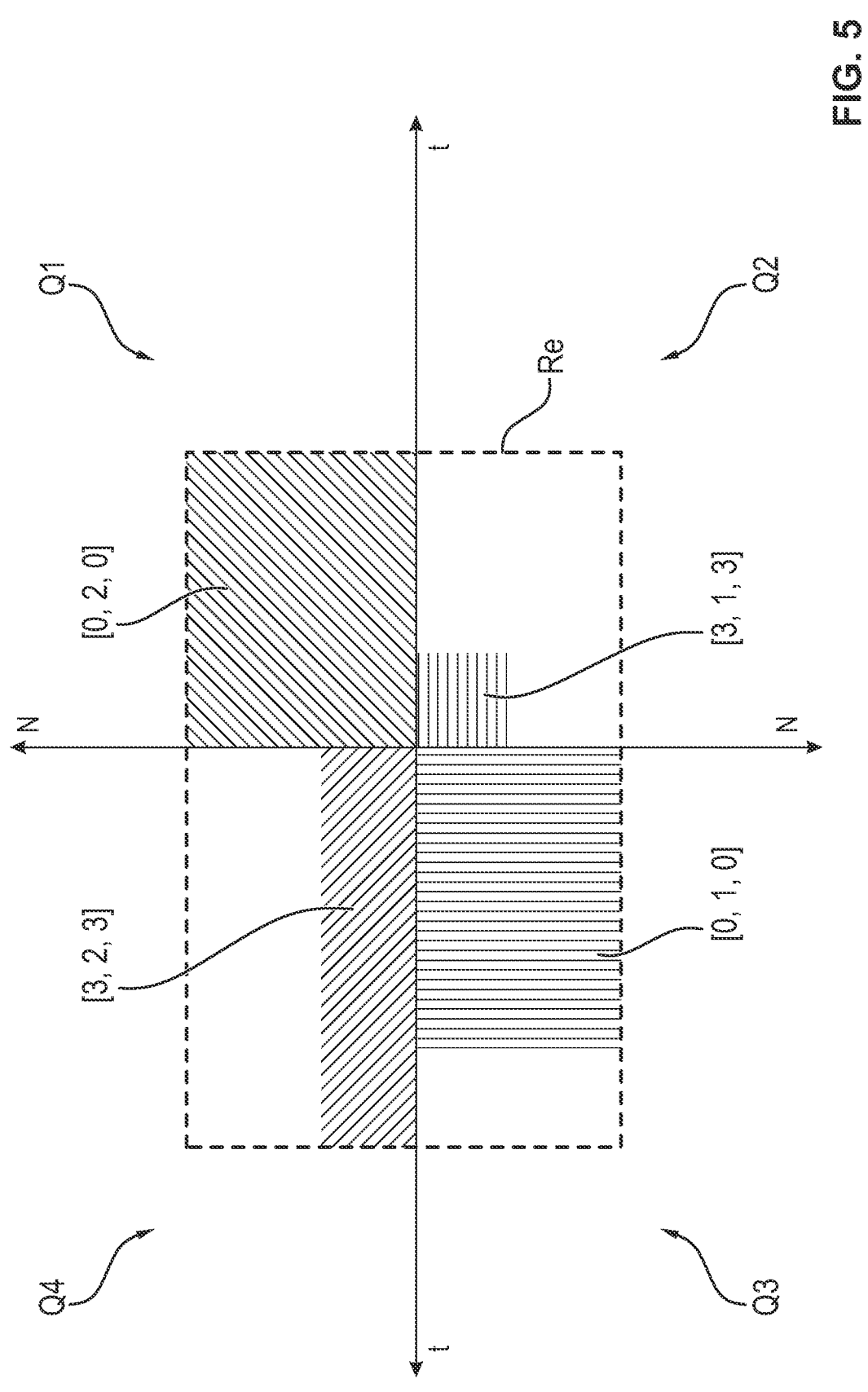
FIG. 5 is an exemplary presentation of the frequency of four asynchrony sequences, which are time asynchronies.
Figure 6:
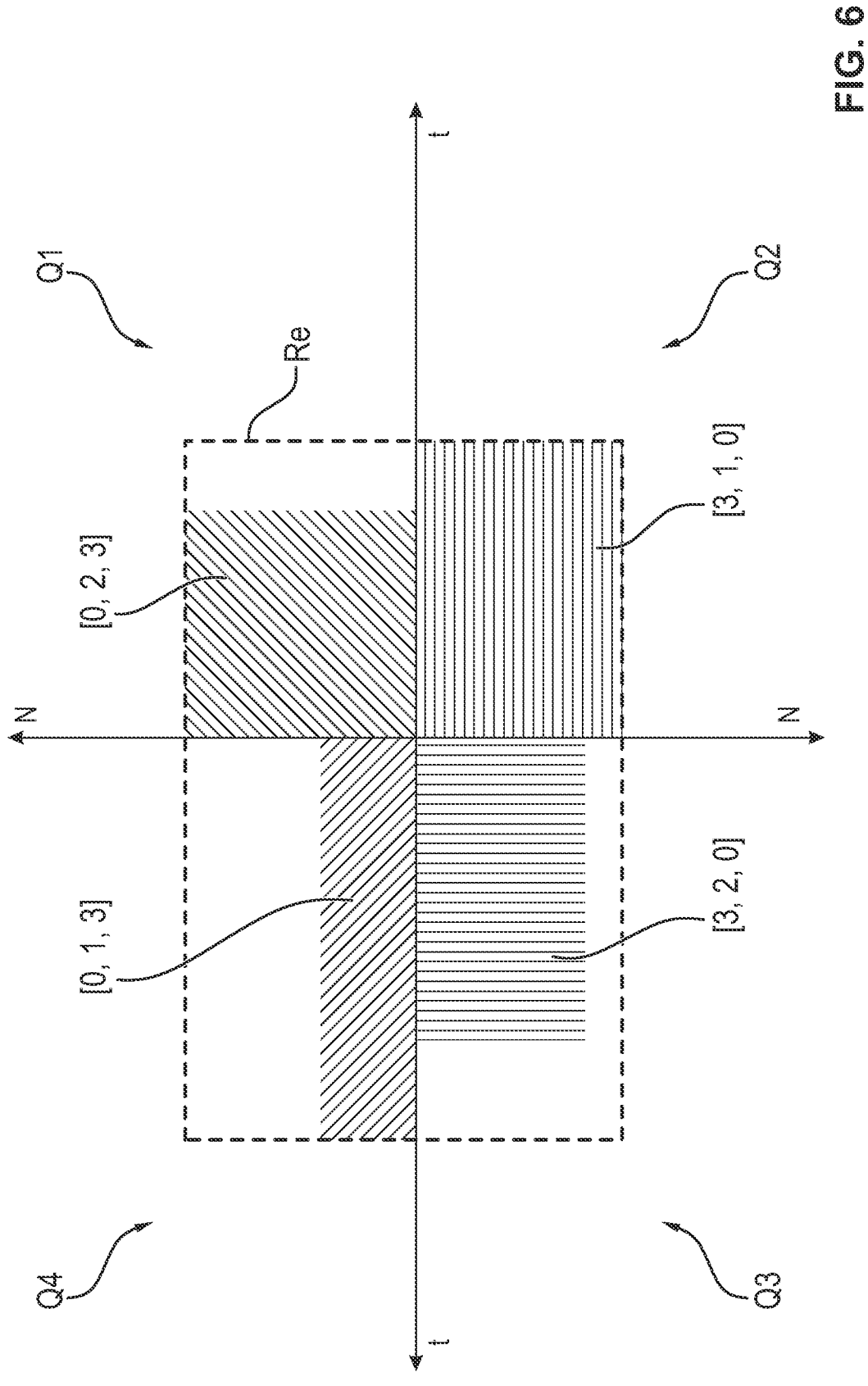
FIG. 6 is an exemplary presentation of the frequency of four asynchrony sequences, which are event asynchronies.

FIG. 5 and FIG. 6 show examples of how a result obtained by the monitoring unit 11 is output on the display and control unit 12. The upper half of the illustration shows inspiratory asynchrony sequences, and the lower half shows expiratory asynchrony sequences. In an inspiratory asynchrony sequence, an inspiratory effort is not completely overlapped in time by a ventilation stroke, and in an expiratory asynchrony sequence, a ventilation stroke is not completely overlapped in time by an inspiratory effort. The left half of the illustration refers to asynchronies caused by an activity of the ventilator 100 triggered too early or incorrectly. Accordingly, the right half refers to too late or no activity caused by the ventilator 100. The terms "too early", "too late", "erroneously" and "absent" refer to the view of the patient Pt.

FIG. 5 shows an example of how the four event asynchronies are output. FIG. 6 shows an example of how the four time asynchronies are output. In the example shown, the display area used is divided into four quadrants Q1 to Q4. In both FIG. 5 and FIG. 6, quadrants Q1 and Q4 represent two different inspiratory asynchrony sequences, while the other two quadrants Q2 and Q3 represent two different expiratory asynchrony sequences. Of course, the asynchrony sequences can also be distributed differently among the four quadrants.

Quadrants Q3 and Q4 in FIG. 6 represent asynchrony sequences due to ventilation strokes executed too early, quadrants Q1 and Q2 represent asynchrony sequences due to ventilation strokes executed too late. Quadrant Q4 illustrates the asynchrony sequence [0,1,3] (reverse triggering), quadrant Q1 illustrates the asynchrony sequence [0,2,3] (late triggering), quadrant Q3 illustrates the asynchrony sequence [3,2,0] (premature cycling off), and quadrant Q2 illustrates the asynchrony sequence [3,1,0] (late cycling off).

In the example of FIG. 5, quadrants Q3 and Q4 represent asynchrony sequences with additional, i.e. spurious, activities of the ventilator 100. These spurious activities can be described as extreme cases of "too early". Quadrant Q1 illustrates the asynchrony sequence [0,2,0] (Missed Effort), quadrant Q2 illustrates the asynchrony sequence [3,1,3] (Missed Expiration), quadrant Q3 illustrates the asynchrony sequence [0,1,0] (Auto Triggering), and quadrant Q4 illustrates the asynchrony sequence [3,2,3] (Double Triggering). In these four asynchrony sequences, the ventilator 100 did not detect an actually executed inspiratory effort of the patient Pt and therefore did not execute a ventilation stroke, or erroneously detected an inspiratory effort and thereupon executed a ventilation stroke, or erroneously did not detect that the patient Pt had completed an inspiratory effort, or erroneously completed a ventilation stroke.

In the example of FIG. 5 as well as in the example of FIG. 6, the x-axis shows the mean duration of the asynchrony sequences of the respective type in [sec] or the mean proportion of the total duration of artificial ventilation so far, e.g. in [%] since the time when the artificial ventilation of this patient Pt was started or since the last calibration or adjustment of the ventilator 100, the mean duration being calculated per arithmetic mean or per median. On the y-axis, the frequency of asynchrony sequences of each type is plotted in [number/min] or as a proportion in [%] of the ventilation strokes performed. The area for an asynchrony type sequence is larger the longer and/or more frequently this asynchrony sequence has occurred in total, and shows, for example, the total duration of the respective asynchrony sequence. It is possible to indicate the respective asynchrony type sequence by a color or by other coding perceptible by a human. Of course, it is possible that at least one asynchrony sequence does not occur at all and therefore the corresponding rectangle is missing.

In the two examples shown, the averaged duration in [min] is entered on the x-axis, and the frequency, i.e. number per minute, is entered on the y-axis. It is also possible to use a different measure on the x-axis for how long the asynchrony sequences of the respective type occurred, and on the y-axis a different measure for how seriously an asynchrony sequence affected the supportive artificial ventilation.

In one embodiment, at least one pneumatic sensor 2, 3, 7, 15 measures a pneumatic measure for the patient Pt's own respiratory activity and/or the assisted artificial ventilation provided by the ventilator 100. The signal from this pneumatic sensor 2, 3, 7, 15 can be used to derive the mechanical effort exerted by the patient Pt's own respiratory muscles (work of breathing) or the pressure integrated over time (pressure-to-product). In one embodiment, the respective mechanical respiratory effort or the integrated pressure is plotted on the y-axis for each asynchrony sequence.

In one embodiment, an overall rectangle Re is placed around the maximum four individual rectangles for the four asynchrony sequences, cf. FIG. 5 and FIG. 6. The overall rectangle Re encloses all of these four individual rectangles and is as small as possible. The size of the overall rectangle Re is another visually perceptible measure of how well the ventilation strokes are synchronized with the patient's own respiratory activity. This size can be quickly perceived visually.

While specific embodiments of the invention have been shown and described in detail to illustrate the application of the principles of the invention, it will be understood that the invention may be embodied otherwise without departing from such principles.

List of reference signs

| 2 | Pneumatic respiratory sensor in front of the patient Pt's mouth, measures the airway pressure $P_{aw}$ and optionally the volumetric flow Vol', acts as the airway pressure sensor, comprises components 2.1 and 2.2 |
| 2.1 | Respiratory sensor 2 transducer, taps a gas sample from the fluid connection between the patient Pt's lungs Lu and the ventilator 100 |
| 2.2 | Actual pressure sensor of the respiration sensor 2 |
| 3 | Probe in the esophagus Sp of the patient Pt, measures the esophageal pressure $P_{es}$ and optionally the gastral pressure $P_{ga}$, connected to the measuring catheter 6 |
| 4 | Connector in the patient Pt's mouth, connected to the measuring catheter 6 in the esophagus Sp |
| 5.1.1, 5.1.2 | Pair of measuring electrodes close to the heart on the patient's skin Pt |
| 5.2.1, 5.2.2 | Pair of measuring electrodes close to the diaphragm on the patient's skin Pt |
| 6 | Measuring catheter in the esophagus Sp of the patient Pt, connected to the measuring probe 3 and the connector 4 |
| 7 | Gastral probe in the stomach Ma of the patient Pt, measures the gastral pressure $P_{ga}$ |
| 10 | Signal processing unit of the ventilator 100, receives measured values from the respiratory sensors 2, 3, 5.1.1 to 5.2.2, 7, generates at least one respiratory signal $Sig_{res}$ and triggers the ventilation strokes of the ventilator 100 |
| 11 | Signal processing monitoring unit for the ventilator 100, monitors how well the ventilation strokes of the ventilator 100 are synchronized with the patient Pt's own respiratory activity, |

-continued

List of reference signs

| | generates a series of situations, detects asynchrony sequences in the series of situations and causes a presentation of the asynchrony sequences to be output on the display and control unit 12 |
| 12 | Display and control unit of the ventilator 100 |
| 15 | Sensor on ventilator 100, measures the volumetric flow Vol' |
| 100 | Ventilator, artificially ventilates the patient Pt, comprises the display and control unit 12, the signal processing unit 10 and optionally the monitoring unit 11 |
| Atm(1), ..., Atm(4) | Breaths detected in the sum signal $Sig_{Sum}$ |
| Hz(x), Hz(y) | Heartbeats detected in the sum signal $Sig_{Sum}$ |
| Pt | Patient |
| Q1, ..., Q4 | Quadrants of an exemplary presentation visualizing the respective frequency and duration of four asynchrony sequences |
| Re | Total rectangle around the four rectangles in the four quadrants Q1 to Q4 |
| S. 100 | Schematic time course of the ventilation strokes executed by the ventilator 100 |
| S. Pt | Schematic time course of an exemplary respiratory signal correlating with the patient Pt's own respiratory activity |
| $Sig_{res}$ | Pneumatic respiratory signal |
| $Sig_{Sum}$ | Electrical sum signal resulting from a superposition of a cardiogenic signal with an electrical respiratory signal $Sig_{res}$ and generated from measured values of the measuring electrodes 5.1.1 to 5.2.2 |

What is claimed is:

1. A monitoring process for monitoring a ventilator, the process comprising the steps of:

providing a signal-processing monitoring unit for monitoring the ventilator, wherein the ventilator is configured to perform supportive artificial ventilation of a patient, the supportive artificial ventilation including receiving measured values from a sensor arrangement comprising a respiratory sensor configured and arranged to measure a respective indicator which correlates with the patient's own inspiratory efforts, the supportive artificial ventilation further including evaluating measured values of the sensor arrangement to generate a respiratory signal which is an indicator of the patient's own inspiratory efforts, and depending on the respiratory signal, to perform a sequence of ventilation strokes with an objective that a respective start and a respective end of each inspiratory effort of the patient trigger a respective start and a respective end, of exactly one ventilation stroke, wherein at least two possible asynchrony types are predefined, which are different from each other, wherein a predefined possible asynchrony type has actually occurred if a ventilation stroke begins or ends earlier or later than an inspiratory effort triggering this ventilation stroke, or if the ventilation stroke is triggered without the inspiratory effort or if the inspiratory effort does not trigger the ventilation stroke;

the process of monitoring the ventilator with the monitoring unit is performed while the ventilator is performing supportive artificial ventilation of the patient;

the monitoring process further comprising the steps of:

within the monitoring unit, detecting the respective start and the respective end of each inspiratory effort of the patient, wherein the respiratory signal is evaluated for this detection;

within the monitoring unit, determining a respective start and a respective end of each ventilation stroke;

detecting with the monitoring unit any actual occurrence of one of the predefined possible asynchrony types at least if its duration is above a predefined asynchrony duration threshold; and within the monitoring unit, determining a respective measure for a frequency and/or a duration of the actual occurrence of each predefined possible asynchrony type occurring during the sequence of ventilation strokes;

wherein a time asynchrony occurs if a ventilation stroke begins or ends earlier or later than the inspiratory effort triggering the ventilation stroke, wherein an event asynchrony occurs if a ventilation stroke is triggered without an inspiratory effort or an inspiratory effort does not trigger a ventilation stroke, wherein a presentation is generated and provided as an output in a form configured to be perceptible by a human, wherein the presentation is generated using two axes, wherein the two axes are perpendicular or oblique to each other and wherein a two-dimensional area is shown for each asynchrony type in the presentation, wherein the two dimensions of the two-dimensional area depend on the measure for frequency and the measure for duration, respectively.

2. The monitoring process of claim 1, further comprising:

within the monitoring unit, determining which one of four possible situations is present at a sampling time point, the four possible situations comprising:

the patient performs the inspiratory effort, and the ventilator performs the ventilation stroke;

neither the patient performs the inspiratory effort nor does the ventilator perform the ventilation stroke;

the patient performs the inspiratory effort, and the ventilator does not perform the ventilation stroke; and the ventilator performs the ventilation stroke, and the patient does not perform the inspiratory effort, for determining which situation is present at the sampling time point, evaluating the respiratory signal, wherein the step of determining the measures for the frequency and/or the duration of the predefined possible asynchrony types comprises the step of determining a series of situations, wherein the series of situations comprises one situation per sampling time point of the series of sampling time points, wherein, in the series of situations, a situation sequence is determined, wherein a determined situation sequence comprises at least two different immediately successive situations of the series of situations which successive situations differ from each other, and wherein for each predefined possible asynchrony type, the measure for a frequency of asynchrony and/or the measure for a duration of asynchrony is determined by using the determined situation sequences in which the predefined possible asynchrony type is actually present.

3. The monitoring process of claim 2, wherein the measure for the frequency and/or the duration of each predefined possible asynchrony type is determined by the monitoring unit depending on the respective frequency and/or duration of the determined situation sequences in which this asynchrony type is present.

4. The monitoring process according to claim 1, wherein:

the ventilator is adapted to automatically detect when the patient starts and stops the inspiratory effort;

the ventilator is configured to apply a decision rule to the respiratory signal for detecting the inspiratory effort start and stop, said decision rule depends on a parameter;

the monitoring process further comprises the steps of:

with the monitoring unit, calculating a target setpoint for the parameter of the decision rule, the target setpoint is calculated depending on at least one determined measure for a frequency and/or a duration of a possible asynchrony type; and transmitting a message to the ventilator or outputting the message in a form configured to be perceptible by a human, wherein the message comprises information about the calculated target setpoint and/or about a change in a currently used setpoint of the parameter wherein the change depends on the target setpoint, and changing the applied decision rule of the ventilator in response to the received message or to a user input.

5. The monitoring process according to claim 1, further comprising:

with the monitoring unit, generating the presentation that shows the respective determined measures for the frequency and/or the duration of at least two of the predefined possible asynchrony types having occurred during the sequence of ventilation strokes; and triggering the step that the generated presentation is output in the form configured to be perceived by a human.

6. The monitoring process according to claim 5, wherein:

for each predefined asynchrony type, which is shown in the presentation, a measure for the frequency and a measure for the duration of the predefined asynchrony type are determined; and for each of the presented predefined asynchrony types both measures are shown in the presentation.

7. The monitoring process according to claim 6, wherein:

a measure for the frequency of the respective predefined possible asynchrony type is plotted on one axis and a measure for the duration of the same predefined possible asynchrony type is plotted on the other axis; and each of the asynchrony types shown in the presentation is shown by means of a rectangular or trapezoidal surface area, with two dimensions of this area depending upon the two measures.

8. The monitoring process according to claim 1, wherein the monitoring unit detects any occurrence of the following eight predefined possible asynchrony types at least if occurring above a predefined asynchrony duration threshold:

the ventilation stroke triggers the inspiratory effort (reverse triggering);

the ventilation stroke is triggered too late (late triggering);

the ventilation stroke is ended too late (late cycling off);

the ventilation stroke is ended too early (premature cycling off);

the ventilation stroke is triggered without the inspiratory effort (auto triggering);

the inspiratory effort does not trigger the ventilation stroke (missed effort);

a first inspiratory effort is terminated during the ventilation stroke, and a second inspiratory effort is started during the same ventilation stroke (missed expiration); and a first ventilation stroke is completed during an inspiratory effort, and a second ventilation stroke is started during the same inspiratory effort (double triggering).

9. The monitoring process according to claim 8, wherein the monitoring unit:

generates a first presentation which refers to first four of the eight predefined possible asynchrony types; and/or generates a second presentation, which refers to remaining four of the eight predefined possible asynchrony types;

wherein the monitoring unit causes the first presentation and/or the second presentation to be output in a form configured to be perceptible by a human, wherein depending on a user input, either the first presentation or the second presentation or both presentations are output.

10. A computer program on a non-transitory computer-readable medium, the computer program being executable on a signal-processing monitoring unit with a data communication with a ventilator, the ventilator configured to perform supportive artificial ventilation of a patient, the ventilator configured during the supportive artificial ventilation to receive measured values from a sensor arrangement comprising a respiratory sensor configured and arranged to measure a respective indicator which correlates with the patient's own inspiratory efforts;

to generate a respiratory signal, which is an indication of the patient's own inspiratory effort, generating the signal by evaluating the measured values of the sensor arrangement;

depending on the respiratory signal, to perform a sequence of ventilation strokes with an objective that a respective start and a respective end of each inspiratory effort of the patient trigger a respective start and a respective end of exactly one ventilation stroke, wherein at least two possible asynchrony types are pre-defined, which are different from each other, wherein a predefined possible asynchrony type has actually occurred if a ventilation stroke begins or ends earlier or later than an inspiratory effort triggering this ventilation stroke, or if the ventilation stroke is triggered without the inspiratory effort or if the inspiratory effort does not trigger the ventilation stroke;

with execution of the computer program on the signal-processing monitoring unit, the computer program causes the signal-processing monitoring unit to:

monitor the ventilator with the monitoring unit while the ventilator is performing supportive artificial ventilation of the patient;

detect the respective start and the respective end of each inspiratory effort of the patient, wherein the respiratory signal is evaluated for the detection;

determine a respective start and end of each ventilation stroke;

detect any actual occurrence of each predefined possible asynchrony type at least if its duration is above a predefined asynchrony duration threshold; and determine a measure for a respective frequency and/or a respective duration of the actual occurrence of each predefined possible asynchrony type occurring during the sequence of ventilation strokes, wherein a time asynchrony occurs if a ventilation stroke begins or ends earlier or later than the inspiratory effort triggering the ventilation stroke, wherein an event asynchrony occurs if a ventilation stroke is triggered without an inspiratory effort or an inspiratory effort does not trigger a ventilation stroke,

26 wherein a presentation is generated and provided as output in a form configured to be perceptible by a human, wherein the presentation is generated using two axes, wherein the two axes are perpendicular or oblique to each other, wherein a two-dimensional area is shown for each asynchrony type in the presentation, wherein the two dimensions of the two-dimensional area depend on the measure for frequency and the measure for duration, respectively.

11. A ventilating process for supportive artificial ventilation of a patient by a ventilator, the ventilating process comprising the steps of:

providing a signal-processing monitoring unit;

during supportive artificial ventilation, receiving with the ventilator measured values from a sensor arrangement comprising a respiratory sensor configured and arranged to measure a respective indicator which correlates with the patient's own inspiratory efforts;

generating with the ventilator a respiratory signal, which respiratory signal is an indicator for the patient's own inspiratory effort, the respiratory signal is generated by evaluating the measured values;

with the ventilator, performing a sequence of ventilation strokes based on the respiratory signal with an objective that a respective start and a respective end of each inspiratory effort of the patient trigger a respective start and a respective end of exactly one ventilation stroke, wherein at least two possible asynchrony types are pre-defined, which are different from each other, wherein a predefined possible asynchrony type has actually occurred if a ventilation stroke begins or ends earlier or later than an inspiratory effort triggering this ventilation stroke, or the ventilation stroke is triggered without the inspiratory effort or the inspiratory effort does not trigger the ventilation stroke;

with the monitoring unit, detecting the respective start and the respective end of each inspiratory effort of the patient, wherein the respiratory signal is evaluated for the detection;

with the monitoring unit, determining a respective start and a respective end of each ventilation stroke;

with the monitoring unit, detecting every actual occurrence of each predefined possible asynchrony type at least if its duration is above a predefined asynchrony duration threshold; and with the monitoring unit, determining a respective measure for a frequency and/or a respective duration of the actual occurrence of each predefined possible asynchrony type occurring during the sequence of ventilation strokes, wherein a time asynchrony occurs if a ventilation stroke begins or ends earlier or later than the inspiratory effort triggering the ventilation stroke, wherein an event asynchrony occurs if a ventilation stroke is triggered without an inspiratory effort or an inspiratory effort does not trigger a ventilation stroke, wherein a presentation is generated and provided as output in a form configured to be perceptible by a human, wherein the presentation is generated using two axes, wherein the two axes are perpendicular or oblique to each other, wherein a two-dimensional area is shown for each asynchrony type in the presentation and wherein the two dimensions of the two-dimensional area depend on the measure for frequency and the measure for duration, respectively.

12. A signal-processing monitoring unit for monitoring a ventilator, wherein the ventilator is configured to perform supportive artificial ventilation of a patient, the supportive artificial ventilation including receiving measured values from a sensor arrangement comprising a respiratory sensor configured and arranged to measure a respective indicator which correlates with the patient's own inspiratory efforts, wherein the ventilator is configured to generate a respiratory signal, which is an indicator of the patient's own inspiratory effort by evaluating the measured values, wherein the ventilator is configured to perform, depending on the respiratory signal, a sequence of ventilation strokes with an objective that a respective start and a respective end of each inspiratory effort of the patient trigger a respective start and a respective end of exactly one ventilation stroke, wherein at least two possible asynchrony types are predefined, which are different from each other, wherein a predefined possible asynchrony type has actually occurred if a ventilation stroke begins or ends earlier or later than an inspiratory effort triggering the ventilation stroke, or the ventilation stroke is triggered without the inspiratory effort or the inspiratory effort does not trigger the ventilation stroke, wherein the monitoring unit is configured to:

detect the respective start and the respective end of each inspiratory effort of the patient by evaluating the respiratory signal;

determine a respective start and a respective end of each ventilation stroke;

detect any actual occurrence of one of the predefined possible asynchrony types at least if its duration is above a predefined asynchrony duration threshold; and determine a measure for a frequency and/or a duration of the actual occurrence of each predefined possible asynchrony type occurring during a sequence of ventilation strokes, wherein a time asynchrony occurs if a ventilation stroke begins or ends earlier or later than the inspiratory effort triggering the ventilation stroke, wherein an event asynchrony occurs if a ventilation stroke is triggered without an inspiratory effort or an inspiratory effort does not trigger a ventilation stroke, wherein a presentation is generated and provided as output in a form configured to be perceptible by a human, wherein the presentation is generated using two axes, wherein the two axes are perpendicular or oblique to each other, wherein a two-dimensional area is shown for each asynchrony type in the presentation and wherein the two dimensions of the two-dimensional area depend on the measure for frequency and the measure for duration, respectively.

13. The monitoring unit according to claim 12, wherein the monitoring unit is configured to:

determine which one of following four possible situations exists at a sampling time point:

the patient performs the inspiratory effort, and the ventilator performs the ventilation stroke;

neither the patient performs the inspiratory effort nor does the ventilator perform the ventilation stroke;

the patient performs the inspiratory effort, but the ventilator does not perform the ventilation stroke;

the ventilator performs the ventilation stroke, but the patient does not perform the inspiratory effort, wherein the monitoring unit is configured to use the respiratory signal for determining if and which one of the four possible situations is present at a sampling time point, wherein the monitoring unit is configured, in determining the measures of the frequency and/or the duration for each of the predefined possible asynchrony types, to determine a series of situations, wherein the series of situations comprises one situation per each sampling time point of the series, wherein in the series of situations, the monitoring unit is configured to determine a situation sequence, wherein a determined situation sequence comprises at least two different immediately successive situations which differ from each other, and wherein the monitoring unit is configured, for each predefined possible asynchrony type, to determine the measure for the frequency and/or duration of the predefined possible asynchrony type using those determined situation sequences in which that asynchrony type is actually present.

14. The monitoring unit according to claim 12, wherein:

the ventilator is configured to apply a decision rule to the respiratory signal, to decide when the patient starts and stops the inspiratory effort, said decision rule depending on a parameter;

the monitoring unit is configured to:

calculate a target setpoint for the parameter of the decision rule; and cause a message to be transmitted to the ventilator or output in a form perceptible by a human;

wherein the message comprises information about the calculated target setpoint and/or about a change in a currently used setpoint of the parameter;

the ventilator is configured to automatically change the applied decision rule in response to the received message or on a user input.

15. A ventilation arrangement comprising:

a sensor arrangement comprising one or more respiratory sensors configured and arranged to measure a respective indicator which correlates with the patient's own inspiratory efforts to provide measured values;

a ventilator configured to perform supportive artificial ventilation of the patient, and while doing so receive the measured values from the sensor arrangement to generate a respiratory signal, which is an indicator of the patient's own inspiratory effort, wherein the ventilator is configured, depending on the respiratory signal, to perform a sequence of ventilation strokes with an objective that a respective start and a respective end of each inspiratory effort of the patient trigger a respective start and a respective end of exactly one ventilation stroke, wherein at least two possible asynchrony types are predefined, which are different from each other, wherein a predefined possible asynchrony type has actually occurred if a ventilation stroke begins or ends earlier or later than an inspiratory effort triggering this ventilation stroke, or the ventilation stroke is triggered without the inspiratory effort or if the inspiratory effort does not trigger the ventilation stroke; and a signal-processing monitoring unit configured to:

detect a respective start and a respective end of each inspiratory effort of the patient by evaluating the respiratory signal;

determine the respective start and end of each ventilation stroke;

detect any occurrence of one of the predefined possible asynchrony types at least if its duration is above a predefined asynchrony duration threshold; and determine a measure for a respective frequency and/or a respective duration of the actual occurrence of each predefined possible asynchrony type occurring during a sequence of ventilation strokes, wherein a time asynchrony occurs if a ventilation stroke begins or ends earlier or later than the inspiratory effort triggering the ventilation stroke, wherein an event asynchrony occurs if a ventilation stroke is triggered without an inspiratory effort or an inspiratory effort does not trigger a ventilation stroke, wherein a presentation is generated and provided as output in a form configured to be perceptible by a human, wherein the presentation is generated using two axes, wherein the two axes are perpendicular or oblique to each other, wherein a two-dimensional area is shown for each asynchrony type in the presentation and wherein the two dimensions of the two-dimensional area depend on the measure for frequency and the measure for duration, respectively.

16. The ventilation arrangement according to claim 15, wherein:

the monitoring unit is a component of the ventilator; and the ventilator further comprises a further signal-processing unit configured:

to receive the measured values from the sensor arrangement and to generate the respiratory signal by evaluating the measured values; and to trigger the sequence of ventilation strokes.

\* \* \* \* \*